United States Patent [19]

Schütze et al.

[11] Patent Number: 4,981,997

[45] Date of Patent: Jan. 1, 1991

[54] PROCESS FOR THE PREPARATION OF 2,5-DIARYLAMINOTEREPHTHALIC ACIDS

[75] Inventors: Detlef-Ingo Schütze, Cologne; Reinold Schmitz, Odenthal, both of Fed. Rep. of Germany

[73] Assignee: Bayer Aktiengesellschaft, Leverkusen, Fed. Rep. of Germany

[21] Appl. No.: 414,825

[22] Filed: Sep. 29, 1989

[30] Foreign Application Priority Data

Oct. 12, 1988 [DE] Fed. Rep. of Germany ....... 3834747

[51] Int. Cl.$^5$ .............................................. C07C 51/21
[52] U.S. Cl. ...................................... 562/421; 560/44; 562/457
[58] Field of Search .................... 562/457, 421; 560/44

[56] References Cited

U.S. PATENT DOCUMENTS 3,388,149  6/1968  Dien ................................ 562/457 X

FOREIGN PATENT DOCUMENTS 1144285  2/1963  Fed. Rep. of Germany .
1147953  5/1963  Fed. Rep. of Germany .
 907808 10/1962  United Kingdom .
 975466 11/1964  United Kingdom .
1228727  4/1971  United Kingdom .

*Primary Examiner*—Werren B. Lone
*Assistant Examiner*—Vera C. Clarke
*Attorney, Agent, or Firm*—Sprung Horn Kramer & Woods

[57] ABSTRACT

A process for the preparation of 2,5-diarylaminoterephthalic acids by oxidation of 2,5-diarylamino-3,6-dihydroterephthalic acid esters using oxygen or oxygen-containing gases, preferably air, in alcoholic-alkaline or alcoholic-aqueous-alkaline solution or suspension in the presence of an oxygen-transferring agent and working up to give the 2,5-diarylaminoterephthalic acids, characterized in that the oxidation is carried out in the presence of quaternary ammonium compound.

20 Claims, No Drawings

PROCESS FOR THE PREPARATION OF 2,5-DIARYLAMINOTEREPHTHALIC ACIDS

The invention relates to a process for the preparation of 2,5-diarylaminoterephthalic acids, the important intermediates for the preparation of the useful violet or red quinacridone pigments.

According to Liebermann (Liebigs Annalen Volume 404 (1914), p. 272), the 2,5-diarylaminoterephthalic acids are obtained by oxidation of 2,5-diarylamino-3,6-dihydroterephthalic acid dialkyl esters using iodine in alcoholic solution or using atmospheric oxygen in glacial acetic acid/alcohol and by hydrolysis of the 2,5-diarylaminoterephthalic acid dialkyl esters thus obtained and isolated using alcoholic-aqueous liquor In BE-PS 579,621, a simplified process was then described, in which the 2,5-diarylamino-3,6-dihydroterephthalic acid dialkyl esters are oxidized in aqueous-alcoholic liquor and simultaneously hydrolysed to the 2,5-diarylaminoterephthalic acids in a single reaction step. Sodium m-nitrobenzenesulphonate is used as the oxidizing agent here. In this connection, at least 1 mole of the oxidizing agent is necessary per mole of the 2,5-diarylamino-3,6-dihydroterephthalic acid ester employed. In addition, it is mentioned that, instead of sodium m-nitrobenzenesulphonate, atmospheric oxygen can also be used as the oxidizing agent. However, the process is then much less effective and considerably more difficult to control (see BE-PS 579,621, p. 7, para. 2, lines 8 to 11). Further aromatic nitro compounds such as, for example, m-dinitrobenzene, p-nitrotoluene, p-nitrochlorobenzene etc. are also described as oxidizing agents in aqueous-alcohlic liquors (US-PS 3,388,149).

In order to be able to avoid the use of aromatic nitro compounds, further experiments were undertaken to develop a process for the oxidation using air. In DE-AS (German Published Specification) 1,118,215, the oxidation of the 2,5-diarylamino-3,6-dihydroterephthalic acid dialkyl esters is carried out directly using air after their formation from succinylosuccinic acid dialkyl esters and the respective arylamine in excess arylamine. In an additional step, the resultant 2,5-diarylaminoterephthalic acid dialkyl esters isolated must be hydrolysed to the 2,5-diarylaminoterephthalic acid. This process is very complicated.

A process was then disclosed in DE-AS (German Published Specification) 1,114,285 in which the oxidation of the 2,5-diarylamino-3,6-dihydroterephthalic acid dialkyl esters is carried out using air in aqueous-alcoholic liquors with the addition of small amounts of quinonesulphonic acids, such as naphthoquinone-, anthraquinone- and phenanthrenequinonesulphonic acids, as oxygen transferrers. This process undergoes a broadening through DE-AS (German Published Specification) 1,147,953 in which quinones such as anthraquinone, phenanthrenequinone, naphthoquinone, chloranil or quinonecarboxylic acids are used directly as oxygen transferrers. Compared to the other process, it is true that this air oxidation process represents a considerable improvement, but it may not be satisfactory, in particular for the preparation of the substituted 2,5-dianilinoterephthalic acids such as, for example, di-4-toluidino- or di-4-chloroanilinoterephthalic acids. In order to prepare these two substituted 2,5-diarylaminoterephthalic acids, n-butanol/water is employed as the solvent since the oxidation cannot be carried out completely in methanol/water or ethanol/water using air. However, in n-butanol/water, a multiphase system is formed, by means of which, for example in the reworking of Example 2 of DE-AS (German Published Specification) 1,144,285, a very oily and agglomerated product is formed. In addition, a considerably longer oxidation time is required due to this multiphase system, as has already been indicated. The yields in both published specifications vary between 86% 93%, depending on the derivative.

Surprisingly, the process according to the invention leads with high yields to 2,5-diarylaminoterephthalic acids of high purity with considerably shorter oxidation times. The process according to the invention for the preparation of 2,5-diarylaminoterephthalic acids by oxidation of 2,5-diarylamino-3,6-dihydroterephthalic acid esters with oxygen or oxygen-containing gases, preferably air, in alcoholic-alkaline or alcoholic-aqueous-alkaline solution or suspension in the presence of an oxygen-transferring agent and working up to give the 2,5-diarylaminoterephthalic acids is characterized in that the oxidation is carried out in the presence of a quaternary ammonium compound. An embodiment of this process consists in employing the 2,5-diarylamino-3,6-dihydroterephthalic acid ester formation mixture in the oxidation, as it is obtained in the reaction of 1 mole of succinylosuccinic acid ester with 2 moles of an arylamine, preferably in alcoholic solution.

The oxidations are preferably carried out at 70 to 130° C., particularly preferably at the boiling point of the reaction mixture. If appropriate, the oxidations can be carried out under pressure.

The new process is used in particular for the preparation of 2,5-diarylaminoterephthalic acids of the formula

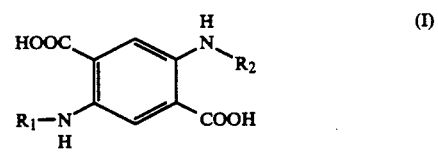

in which

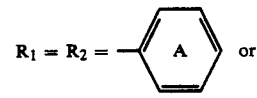

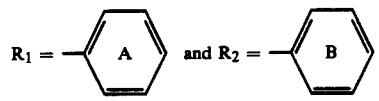

where the rings A and B may be substituted by 1 to 4 substituents from the series comprising $C_1$–$C_4$-alkyl, chlorine, fluorine, $C_1$–$C_4$-alkoxy, carbamoyl which is optionally monosubstituted or disubstituted by $C_1$–$C_4$-alkyl, trifluoromethyl, carboxyl or nitro, or may be fused to an aromatic or heteroaromatic ring, 2,5-diarylamino-3,6-dihydroterephthalic acid esters of the formula

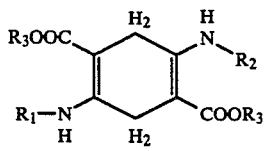

(II)

in which $R_1$ and $R_2$ have the abovementioned meanings and $R_3$ represents alkyl, preferably $C_1$–$C_6$-alkyl, for example methyl, ethyl or i-propyl, or corresonding formtion mixtures preferably being employed in the oxidation.

The process according to the invention can be carried out, for example, as follows: the 2,5-diarylamino-3,6-dihydroterephthalic acid ester is suspended in a mixture consisting of an alcohol and an alkali metal hydroxide or consisting of an alcohol, water and an alkali metal hydroxide, an oxygen transferrer, for example anthraquinonesulphonic acid and, additionally, a quaternary ammonium compound are added, the mixture is heated and oxidized, if appropriate under pressure, by passing through oxygen or oxygen-containing gases, for example, air.

A further embodiment of the new process consists in adding an alkali metal hydroxide or a solution of an alkali metal hydroxide in water, an oxygen transferrer, for example anthraquinonesulphonic acid and a quaternary ammonium compound to the formation mixture for the preparation of the 2,5-diarylamino-3,6-dihydroterephthalic acid esters, which consists of succinylosuccinic acid ester, arylamine, alcohol and, for example, some glacial acetic acid for the condensation, heating the mixture and oxidizing, if appropriate under pressure, by passing through oxygen or oxygen-containing gases, such as, for example, air.

Aniline, p-toluidine, p-chloroaniline, p-anisidine or p-phenetidine are preferably employed as arylamines. Sodium hydroxide and potassium hydroxide are particularly preferably employed as alkali metal hydroxides.

Possible alcohols are preferably methanol, ethanol, propanol, i-propanol, n-butanol, glycols or glycol ethers, for example ethylene glycol, ethylene glycol monomethyl ether and polyglycols and also mixtures of these alcohols.

Oxygen-transferring agents which are preferably employed are: quinones such as anthraquinone, phenanthrenequinone, naphthoquinone and chloranil and their sulphonic and carboxylic acids, which can also be used as salts. The use of anthraquinone mono- and disulphonic acids, or their salts, is particularly preferred; anthraquinone-2-sulphonic acid (salt) is particularly preferably employed. 0.5 to 5% by weight of oxygen-transferring agent are preferably added, relative to 2,5-diarylamino-3,6-dihydroterephthalic acid ester.

Compounds of the formulae

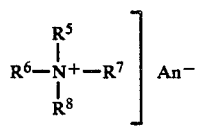

(III)

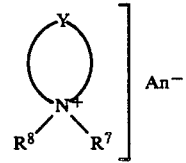

(IV)

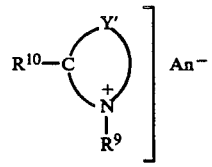

(V)

in which
$R^5$, $R^6$, $R^7$, $R^8$ and $R^9$ signify $C_1$–$C_{54}$ hydrocarbon radicals, the C chain of which may be interrupted by 1 to 15 O atom(s),
$R^{10}$ signifies hydrogen or a substituent, for example $C_1$–$C_4$-alkyl (methyl, ethyl) and
Y and Y' signify the remaining member of a preferably 5-or 6-membered ring, for example a pyridine or imidazole ring, or a ring system and
An⁻ signifies an anionic radical,
are preferably employed as quaternary ammonium compounds.

Radicals $R^5$–$R^9$ which may be mentioned in particular are: $C_1$–$C_{18}$-alkyl, for example methyl, ethyl, dodecyl, cetyl, phenyl, phenyl-$C_1$–$C_{18}$-alkyl, for example benzyl, or —CH$_2$CH$_2$O—(—CH$_2$—CH$_2$O—)$_n$—H with n=0 to 20.

Anionic radicals An⁻ which may be mentioned by way of example are: chloride, sulphate, methylsulphate, benzenesulphonate, toluenesulphonate and hydroxide.

The following may be mentioned in particular: trimethylphenylammonium chloride, triethylphenylammonium chloride, triethylbenzylammonium chloride, trimethylbenzylammonium chloride, dimethyldibenzylammonium chloride, diethyldibenzylammonium chloride, dodecyltrimethylammonium chloride, dodecyldimethylbenzylammonium chloride, with addition products of 5 to 10 moles of ethylene oxide to $C_{16}$–$C_{20}$-alkylamines quaternized with dimethyl or diethyl sulphate, dodecylbenzylalkylamines and dodecylbenzylamine, benzylpyridinium chloride, dodecylpyridinium chloride and cetylpyridinium chloride.

The hydrogensulphates, sulphates, methylsulphates, ethylsulphates, benzene- or toluenesulphonates and hydroxides can be employed instead of the chlorides mentioned with equal effect.

Naturally, &he process according to the invention can also be carried out in the presence of mixtures of quaternary ammonium compounds and/or mixtures of oxygen-transferring agents.

The amounts of quaternary ammonium salts are—relative to the esters to be oxidized—in general between 0.1 and 15, preferably between 0.5 and 8% by weight.

Cationic radicals of the formulae (III) to (V) are, for example: tri-$C_1$–$C_4$-alkyl-phenylammonium, di-$C_1$–$C_4$-alkyl-dibenzylammonium, $C_{10}$–$C_{16}$alkyl-tri-$C_1$–$C_4$-alkylammonium, trialkylammonium polyglycol ether, dialkylbenzylammonium polyglycol ether, alkylbenzylammonium dipolyglycol ether, N-$C_{10}$–$C_{15}$-alkylpyridinium, N-phenyl-$C_7$–$C_{10}$-alkylpyridinium and cationic radicals of quaternization products of $C_1$–$C_4$–trialkylammonium or N–$C_1$–$C_{18}$-alkylimidazolium. The cationic radicals mentioned may be present, for example, in the form of the chlorides, sulphates, methylsulphates, toluenesulphonates, benzenesulphonates or hydroxides. In most cases, hydrolysis to give the 2,5-diarylaminoterephthalic acid takes place at the same time as the oxidation. Otherwise, the hydrolysis can be carried out in the customary manner. A clear solution is formed in many cases. The end of the reaction can be determined chromatographically.

Preferably 1–20 parts by weight, particularly preferably 4 to 12 parts by weight, of solvent and preferably 0.1 to 2.5 parts by weight, particularly preferably 0.3 to 1.5 parts by weight, of alkali, for example NaOH or KOH, are employed relative to 1 part by weight of the 2,5-diarylamino-3,6-dihyd-roterephthalic acid dialkyl ester employed.

The working up of the mixture can be carried out, for example, as follows: the 2,5-diarylaminoterephthalic acids are liberated from the solution of the dialkali metal salts by means of an excess of acid, such as, for example, hydrochloric acid or sulphuric acid, if appropriate after dilution with water and clarifying filtration, and isolated by filtration.

The process according to the invention yields the 2,5-diarylaminoterephthalic acids in very good yields and in very high purity even after very short reaction times. They can be reacted directly to give quinacridone pigments without a further purification, for example by the process mentioned in US-PS 3,342,823.

The process according to the invention is further illustrated by the following examples. The parts and percentage data indicated therein relate to the weight.

EXAMPLE 1

30 parts of diethyl 2,5-dianilino-3,6-dihydroterephthalate, 93 parts of 14% strength sodium hydroxide solution and 1.5 parts of anthraquinone-2-sulphonic acid are introduced into 115 parts of methanol. After addition of 4 parts of a 50% strength solution of dodecylbenzyldimethylammonium chloride in water, the suspension is heated to boiling and 10 l of air/hour are passed through. After 30 minutes, the reaction is complete and solution has occurred.

In order to isolate the product, 90 parts of methanol are first removed by distillation and the remaining reaction solution is rendered acidic to Congo red using 66 parts of 25% strength sulphuric acid. The precipitated product is filtered off with suction, washed with water until neutral and dried.

25.5 parts (=99% of theory) of 2,5-dianilinoterephthalic acid are obtained as a violet, crystalline powder.

If this example is repeated without addition of the quaternary ammonium salt, then 3 hours are required for the oxidation.

EXAMPLE 2

395 parts of methanol, 36 parts of dimethyl succinylosuccinate, 39 parts of aniline and 15.3 parts of glacial acetic acid are heated to 102 to 105° C. for 4 hours in a stirring autoclave.

The reaction mixture is cooled, 42.5 parts of potassium hydroxide dissolved in 79 parts of methanol, 3 parts of anthraquinone-2-sulphonic acid and 5 parts of a 50% strength solution of dodecylbenzyldimethylammonium chloride are added and the mixture is heated to boiling. After the mixture has been oxidized for 3 hours by passing through 10 l of air/hour, it is diluted with 350 parts of water, and the solution is clarified and rendered acidic to Congo red using 95 parts of concentrated hydrochloric acid. The precipitated 2,5-dianilinoterephthalic acid is filtered off with suction, washed with water until neutral and dried.

53.9 parts (=98% of theory) of 2,5-dianilinoterephthalic acid are obtained.

If the same experiment is carried out without addition of the quaternary ammonium salt, then 48.9 parts (=89% of theory) are obtained after 6 hours.

EXAMPLE 3

29.9 parts of dimethyl 2,5-di-4-toluidino-3,6-dihydroterephthalate, 114 parts of 22% strength sodium hydroxide solution and 1.5 parts of anthraquinone-1,5-disulphonic acid are introduced into 152 parts of n-butanol. After addition of 4 parts of a 50% strength solution of dodecylbenzyldimethylammonium chloride in water, the mixture is heated to 80 to 90° C. and oxidized for 7 hours by passing through 10 l of air/hour. About 220 parts of an azeotropic mixture of n-butanol and water are then removed by distillation, about 220 parts of water being added simultaneously. The mixture is then rendered neutral to Congo red using 66 parts of 25% strength sulphuric acid, and the precipitate is filtered off with suction, washed with water until neutral and dried. 27 parts (=97.5% of theory) of 2,5-di-4-toluidinoterephthalic acid as a violet powder. If this example is carried out without addition of the quaternary ammonium salt, a yield of 19.8 parts (=71.5% of theory) is obtained after oxidation.

EXAMPLE 4

410 parts of ethanol, 52.5 parts of p-toluidine, 41.9 parts of dimethyl succinylosuccinate and 17.7 parts of glacial acetic acid are heated to 102 to 105° C. for 4 hours in a stirring autoclave. After cooling, 66 parts of water, 49 parts of potassium hydroxide, 3 parts of anthraquinone-2-sulphonic acid and 2.5 parts of dipolyglycoldodecylbenzylammonium chloride (Soluofen-VV-308 from GAF Corporation) are then added and the mixture is oxidized under reflux for 3 hours using 10 l of air/hour. 300 parts of water are then added, the solution is clarified and the product is precipitated using 89 parts of concentrated hydrochloric acid. After filtering off with suction, washing until neutral and drying, 66.4 parts (=96.1% of theory) of 2,5-di-4-toluidinoterephthalic acid are obtained.

EXAMPLE 5

36 parts of dimethyl succinylosuccinate, 45 parts of p-toluidine and 15 parts of glacial acetic acid are introduced into 315 parts of ethanol. The mixture is stirred at 102 to 105° C. for 4 hours in a stirring autoclave. After cooling, 200 parts of ethanol, 60 parts of water, 42.5 parts of potassium hydroxide, 3 parts of anthraquinone-2-sulphonic acid and 4 g of a 50% strength solution of dodecylbenzydimethyldiammonium chloride in water are added. The mixture is oxidized under reflux for 2.5 hours by passing through 10 l of air/hour. It is then diluted using 300 parts of water, the solution is clarified and the product is precipitated using 83 parts of concentrated hydrochloric acid. After filtering off with suction, washing until neutral and drying, 58 5 parts (=98.5% of theory) of 2,5-di-4-toluidinoterephthalic acid are obtained.

EXAMPLE 6

408 parts of isopropanol, 52.5 parts of p-toluidine, 41.9 parts of dimethyl succinylosuccinate and 18 parts of glacial acetic acid are heated to 102 to 105° C. for 4 hours in a stirring autoclave. After cooling, 66 parts of water, 49 parts of potassium hydroxide, 3 parts of anthraquinone-2-sulphonic acid and 2.5 parts of benzyltriethylammonium chloride are added. The mixture is oxidized under reflux for 3 hours using 10 l of air/hour. After addition of 600 parts of water and clarification, the mixture is rendered neutral to Congo red using 89 parts of concentrated hydrochloric acid. The precipitated product is filtered off with suction, washed with water until neutral and dried. 65.9 parts (=95.4% of theory) of 2,5-di-4-toluidinoterephthalic acid are obtained.

EXAMPLE 7

If Example 6 is repeated and 2.5 g of benzyltrimethylammonium hydroxide are employed instead of 2.5 g of benzyltriethylammonium chloride, then 66.1 parts (=95.7% of theory) of 2,5-di-4-toluidinoterephthalic acid are likewise obtained after an oxidation time of 3 hours.

EXAMPLE 8

95 parts of p-chloroaniline, 72.4 parts of dimethyl succinylosuccinate and 26 parts of glacial acetic acid are stirred in 430 parts of methanol and the mixture is heated to 90 to 95° C. for 4 hours in a stirring autoclave. After cooling, 130 parts of methanol, 183 parts of 45% strength potassium hydroxide solution, 1 part of anthraquinone-2-sulphonic acid and 10 parts of a 50% strength solution of dodecylbenzyldimethylammonium chloride in water are added. The mixture is oxidized for 5 hours at reflux temperature using 10 l of air/hour. 650 parts of water are then added, and the solution is clarified and rendered neutral to Congo red using 160 parts of concentrated hydrochloric acid. After filtering off with suction, washing until neutral and drying, 126.7 parts =95.7% of theory) of red crystalline 2,5-di-4-chloroanilino-terephthalic acid are obtained. If this example is repeated without addition of the quaternary ammonium salt, then 124.2 parts (=93.8% of theory) of 2,5-di-4-chloroanilinoterephthalic acid are obtained after 11 hours.

EXAMPLE 9

620 parts of ethanol, 102 parts of p-anisidine, 81 parts of dimethyl succinylosuccinate and 30 parts of glacial acetic acid are heated to 100 to 103° C. for 5 hours in a stirring autoclave. After cooling, 94 parts of potassium hydroxide, 125 parts of water, 3 parts of anthraquinone-2-sulphonic acid and 5 parts of dipolyglycoldodecylbenzylammonium chloride (Soluofen-VV-308 from GAF Corporation) are added and the mixture is oxidized under reflux for 3 hours using 10 ltr. of air/hour. It is then diluted using 600 parts of water, and the solution is clarified and rendered acidic to Congo red using 155 parts of concentrated hydrochloric acid. The precipitated product is filtered off with suction, washed until neutral and dried. 142 parts (=98% of theory) of violet, crystalline 2,5-di-4-anisidinoterephthalic acid are obtained. If this example is carried out without the addition of the quaternary ammonium salt, then 135 parts (=93.2% of theory) of 2,5-di-4-anisidinoterephthalic acid are obtained after an oxidation time of 10 hours.

We claim:

1. A process for the preparation of a 2,5-diarylaminoterephthalic acid by oxidation of a 2,5-diarylamino-3,6-dihydroterephthalic acid dialkyl ester with oxygen or an oxygen-containing gas in an alcoholic-alkaline or alcoholic-aqueous-alkaline solution or suspension in the presence of an oxygen-transferring agent and liberating the 2,5-diarylaminoterephthalic acid by conducting acidification and filtering, the improvement wherein the oxidation is carried out in the presence of a quaternary ammonium compound.

2. A process according to claim 1 for the preparation of a 2,5-diarylaminoterephthalic acid of the formula (I)

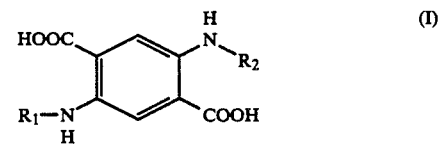

in which,

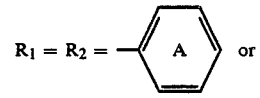

where the rings A and B are unsubstituted or substituted by 1 to 4 substituents selected from the group consisting of $C_1$–$C_4$-alkyl, chlorine, fluorine, $C_1$–$C_4$-alkoxy, carbamoyl which is unsubstituted or monosubstituted or disubstituted by $C_1$–$C_4$-alkyl, trifluoromethyl, carboxyl and nitro, or may be fused to an aromatic or heteroaromatic ring, by oxidation of the 2,5-diarylamino-3,6-dihydroterephthalic acid ester of the formula

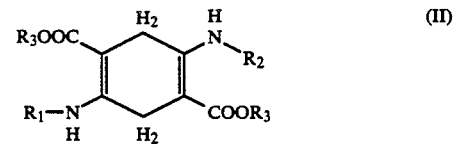

in which $R_1$ and $R_2$ have the abovementioned meanings and $R_3$ represents alkyl.

3. A process according to claim 1, wherein the 2,5-diarylamino-3,6-dihydroterephthalic acid ester formation mixture is employed in the oxidation as it is obtained in the reaction of a succinylsuccinic acid ester with an arylamine.

4. A process according to claim 1, wherein the quaternary ammonium compound of the formulae

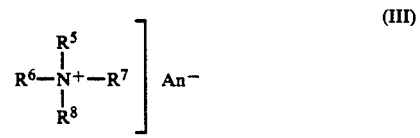

-continued

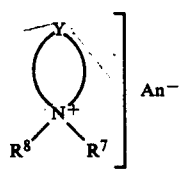 (IV)

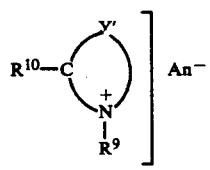 (V)

is employed in which $R^5$, $R^6$, $R^7$, $R^8$ and $R^9$ signify $C_1$–$C_{54}$ hydrocarbon radicals, the C chain of which may be interrupted by 1 to 15 O atom(s), $R^{10}$ signifies hydrogen or a substituent, Y and Y' signify the remaining member of a ring or a ring system and An⁻ signifies and anionic radical.

5. A process according to claim 1, wherein 0.1 to 15% by weight of the quaternary ammonium compound is employed, relative to the 2,5-diarylamino-3,6-dihydroterephthalic acid ester.

6. A process according to claim 1, wherein anthraquinone-2-sulphonic acid is employed as the oxygen-transferring agent.

7. A process according to claim 1, wherein methanol, ethanol or i-propanol is employed as an alcohol in the solution or suspension.

8. A process according to claim 1, wherein the oxidation is carried out at 70 to 130° C.

9. A process according to claim 1, wherein the oxidation is carried out at the boiling point of the reaction mixture.

10. A process according to claim 1, wherein the oxygen-containing gas is air.

11. A process according to claim 1, wherein the acidification is conducted by adding an excess of acid selected from the group consisting of hydrochloric acid and sulphuric acid.

12. A process according to claim 1, wherein the acidification is conducted after dilution with water.

13. A process according to claim 1, wherein the filtering comprises conducting clarifying filtration and isolation by filtration.

14. A process according to claim 4, wherein Y and Y' signify the remaining member of a 5- or 6-membered ring.

15. A process according to claim 5, wherein 0.5 to 8% by weight of the quaternary ammonium compound is employed, relative to the 2,5-diarylamino-3,6-dihydroterephthalic acid ester.

16. A process according to claim 2, wherein $R_3$ is $C_1$–$C_4$-alkyl.

17. A process according to claim 4, wherein $R^{10}$ is $C_1$–$C_4$-alkyl.

18. A process according to claim 4, wherein Y and Y' signify the remaining member of a pyridine ring or an imidazole ring.

19. A process according to claim 4, wherein $R^5$, $R^6$, $R^7$, $R^8$ and $R^9$ signify $C_1$–$C_{18}$-alkyl, phenyl, phenyl-$C_1$–$C_{18}$-alkyl or —$CH_2CH_2O$—(—$CH_2$—$CH_2$)$_n$—H, with n=0 to 20.

20. A process according to claim 4, wherein the anionic radical An⁻ is a chloride, sulphate, methylsulphate, benzenesulphonate, toluenesulphonate or hydroxide.

* * * * *